United States Patent [19]

Maak et al.

[11] Patent Number: 4,552,565
[45] Date of Patent: Nov. 12, 1985

[54] HAIR DYES: DIRESORCYL SULPHIDE, SULPHOXIDE OR SULPHONE COUPLING AGENTS

[75] Inventors: Norbert Maak, Neuss; Edgar Lieske, Duesseldorf, both of Fed. Rep. of Germany

[73] Assignee: Henkel KGaA, Duesseldorf, Fed. Rep. of Germany

[21] Appl. No.: 667,040

[22] Filed: Nov. 1, 1984

[30] Foreign Application Priority Data

Nov. 11, 1983 [DE] Fed. Rep. of Germany ....... 3340829

[51] Int. Cl.$^4$ .......................... A61K 7/13; D06P 1/32; C11D 3/40
[52] U.S. Cl. ............................. 8/409; 8/407; 8/410; 8/412; 568/25; 568/27; 568/28; 568/48
[58] Field of Search ........................... 8/409, 410, 412

[56] References Cited

U.S. PATENT DOCUMENTS

| | | | |
|---|---|---|---|
| 2,760,989 | 8/1956 | Moore | 568/48 |
| 3,006,963 | 10/1961 | Buc et al. | 568/30 |
| 4,003,699 | 1/1977 | Rose et al. | 8/409 |
| 4,129,413 | 12/1978 | Rose et al. | 8/409 |

FOREIGN PATENT DOCUMENTS 1507404 12/1967 France .

OTHER PUBLICATIONS

Chemical Abstracts, 1969, vol. 70, 42849j.
Venkataraman's, "The Chemistry of Synthetic Dyes", vol. V, (Academic Press, 1971), pp. 475–534.
Vol. 53, Journal of American Chemical Society, p. 3466, (1931).

*Primary Examiner*—A. Lionel Clingman
*Attorney, Agent, or Firm*—Ernest G. Szoke; Henry E. Millson, Jr.; Mark A. Greenfield

[57] ABSTRACT

Hair dyes containing oxidation dye precursors in a cosmetic carrier contain as coupler substances compounds corresponding to formula I

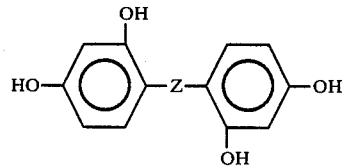

in which Z is a sulfur atom, an >SO group or an >SO$_2$ group or salts thereof. As developer substances, the hair dyes contain the developers normally used in oxidation hair dyes, preferably aromatic and/or heterocyclic diamines or a 2,4,5,6-tetraamino pyrimidine. The new couplers produce color tones in the brown range with good fastness properties and a negligible tendency towards skin staining.

18 Claims, No Drawings

HAIR DYES: DIRESORCYL SULPHIDE, SULPHOXIDE OR SULPHONE COUPLING AGENTS

BACKGROUND OF THE INVENTION

1. Field of the Invention

This invention relates to novel compositions of matter of the developer-coupler type, which are particularly useful as hair dyes, to aqueous preparations of the developer-coupler type for the dyeing of hair and to a process for the dyeing of hair.

2. Description of the Relevant Art

By virtue of their bright colors and good fastness properties, so-called oxidation dyes, formed by the oxidative coupling of one or more developer components with one another or with one or more coupler components, are preferably used for dyeing hair. These hair dyes contain oxidation dye precursors in a cosmetic carrier. The oxidation dye precursors are developer substances and coupler substances which form dyes under the effect of oxidizing agents or atmospheric oxygen. The cosmetic carriers used for the oxidation dye precursors include creams, emulsions, gels, shampoos, foam aerosols, simple solutions, or other preparations which are suitable for application to hair.

The developer substances normally used are primary aromatic amines containing a free or substituted hydroxy or additional amino group in the para- or ortho-position, diamino pyridine derivatives, heterocyclic hydrazone derivatives, 4-amino-pyrazolone derivatives and tetraaminopyrimidines. So-called coupler substances include m-phenylene diamine derivatives, naphthols, rescorcinol derivatives and pyrazolones.

Good oxidation hair dye precursors should satisfy all the following requirements. They should produce a sufficient intensity of the desired color shades when oxidatively coupled. They should attach themselves firmly to human hair without excessively staining the scalp and should be safe and unobjectionable from the toxicological and dermatological points of view.

The use of resorcinol as a coupler is known from German Pat. Nos. 162 625 and 276 761. In addition, other resorcinol derivatives have been proposed as couplers for oxidation hair dyes, including, for example, mono- and dialkyl-m-dihydroxybenzenes (See German Pat. No. 2 617 739, which corresponds to U.S. Pat. No. 4,129,413). However, resorcinol and its derivatives that have previously been used as couplers are unsatisfactory regarding the fastness properties of the hair dyes obtainable therewith.

DESCRIPTION OF THE INVENTION

It has now been found that, through the practice of the present invention, hair dyes containing oxidation dye precursors in a cosmetic carrier, in which the coupler component is at least one compound corresponding to the following formula I

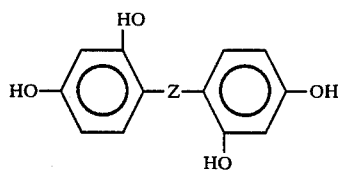

in which Z is a sulfur atom, an >SO group or an >SO₂ group, or cosmetically acceptable salts thereof and in which the developer component is at least one of those normally used in oxidation hair dyes or a salt thereof which is capable of developing a color shade when oxidatively coupled with the coupler of formula I, can satisfy the above-mentioned requirements to a high degree and, quite surprisingly, negligibly stain the skin.

Hair dyes obtained through the practice of the present invention can give particularly bright and intensive dye finishes having high fastness to light and high heat stability and also having tones mainly in the brown region.

The coupler compounds of formula I used in accordance with the present invention are diresorcyl sulfide, diresorcyl sulfoxide and diresorcyl sulfone. The production of diresorcyl sulfide is described in U.S. Pat. No. 2,760,989, specifically incorporated in its entirety by reference herein. As explained generally in U.S. Pat. No. 2,760,989, a solution of sulfur dichloride in an alkyl ether is added to a solution of resorcinol in an alkyl ether at temperatures ranging between 0° and 15° C. The molecular ratio of resorcinol to sulfur dichloride is 2:1. A slight deviation in the amounts of the coreactants will not disturb or hamper the process in any way. Therefore, a slight excess of either one of the reactants may be employed to yield satisfactory results. Within 30 minutes to 1 hour, the condensation reaction is complete and the final product is isolated by any one of the following methods:

(1) Removal of the alkyl ether under reduced pressure, 0–200 mm., and temperature ranging from −25° to 60° C., followed by crystallization from water;

(2) Neutralization of the hydrogen chloride by pouring the reaction solution into sodium carbonate solution or any other aqueous alkali, such as, for example, potassium or lithium carbonate, at temperatures below 25° C., followed by distillation of the ethereal solution at a temperature not exceeding 60° C. and crystallization of the distillation residue from water, the temperature during this operation likewise being kept below 60° C.; and (3) Neutralization of the hydrogen chloride followed by extraction of the product into the aqueous phase by the addition of sodium hydroxide, precipitation of the diresorcyl sulfide with an acid, and crystallization from water.

The production of diresorcyl sulfoxide and sulfone is described in U.S. Pat. No. 3,006,963, specifically incorporated in its entirety by reference herein. As explained generally in U.S. Pat. No. 3,006,963, one mole of diresorcyl sulfide is reacted with one to two moles of hydrogen peroxide in the presence of a catalytic amount of one of the tungstic acids or an alkali metal, alkaline earth metal, ammonium or amine salt of a tungstic acid. The resulting product is diresorcyl sulfoxide. To produce diresorcyl sulfone, one mole of diresorcyl sulfoxide is reacted with hydrogen peroxide in the presence of a catalytic amount of one of the tungstic acids or an alkali metal, alkaline earth metal or amine salt of a tungstic acid.

The production of diresorcyl sulfone is also described in German Patentschrift No. 1 112 282. As explained in German patentschrift No. 1 112 282, the appropriate sulfide is oxidized with hydrogen peroxide in glacial acetic acid in a water bath. The technique is further explained in 53 *Journal of the American Chemical Society* 3466 (1931).

In the practice of the present invention, any developer may be used that will develop a sufficient intensity of the desired color shade when oxidatively coupled with at least one of the coupling components of formula I. Particularly desirable color tones can be obtained when aromatic and/or heterocyclic diamines are contained.

Representative developers such as these include p-phenylene diamine, p-tolylene diamine, N-methyl-p-phenylene diamine, N,N-dimethyl-p-phenylene diamine, N,N-diethyl-2-methyl-p-phenylene diamine, N-ethyl-N-(2-hydroxyethyl)-p-phenylene diamine, chloro-p-phenylene diamine, N,N-bis-(2-hydroxyethyl)-p-phenylene diamine, methoxy-p-phenylene diamine, 2-chloro-o-phenylene diamine, 2,6-dichloro-p-phenylene diamine, 2-chloro-6-bromo-p-phenylene diamine, 2-chloro-6-methyl-p-phenylene diamine, 6-methoxy-3-methyl-p-phenylene diamine, 2,5-diaminoanisole, N-(2-hydroxypropyl)-p-phenylene diamine and N-2-methoxy-ethyl-p-phenylene diamine. In addition, the aromatic and/or heterocyclic diamine developers may contain one or more $NH_2$-groups, NHR-groups or $NR_2$-groups, where R is an alkyl radical containing from 1 to 4 carbon atoms or a hydroxyalkyl radical containing from 2 to 4 carbon atoms.

Other representative developers include N-butyl-N-sulfobutyl-p-phenylene diamine, 2,4,5,6-tetraaminopyrimidine, 4,5-diamino-2,6-bis(methylamino)-pyrimidine, 2,5-diamino-4,6-bis-(methylamino)-pyrimidine, 4,5-diamino-6-(butylamino)-2-(dimethylamino)-pyrimidine, 2,5-diamino-4-(diethylamino)-6-(methylamino)-pyrimidine, 4,5-diamino-6-(diethylamino)-(2-dimethylamino)pyrimidine, 4,5-diamino-2-(diethylamino)-6-(methylamino)-pyrimidine, 4,5-diamino-2-(dimethylamino)-6-(ethylamino)-pyrimidine, 4,5-diamino-2-(dimethylamino)-6-(isopropylamino)-pyrimidine, 4,5-diamino-2-(dimethylamino)-6-(methylamino)-pyrimidine, 4,5-diamino-6-(dimethylamino)-2-(methylamino)-pyrimidine, 4,5-diamino-2-(dimethylamino)-6-(propylamino)-pyrimidine, 2,4,5-triamino-6-(dimethylamino)-pyrimidine, 4,5,6-triamino-2-(dimethylamino)-pyrimidine, 2,4,5-triamino-6-(methylamino)-pyrimidine, 4,5,6-triamino-2-(methylamino)-pyrimidine, 4,5-diamino-2-(dimethylamino)-6-piperidino-pyrimidine, 4,5-diamino-6-(methylamino)-2-piperidino-pyrimidine, 2,4,5-triamino-6-piperidino-pyrimidine, 2,4,5-triamino-6-anilino-pyrimidine, 2,4,5-triamino-6-(benzylamino)-pyrimidine, 2,4,5-triamino-6-(benzylideneamino)-pyrimidine, 4,5,6-triamino-2-piperidino-pyrimidine, 5-amino-2,4,6-tris-(methylamino)-pyrimidine, 2,4,5-triamino-6-(di-n-propylamino)-pyrimidine, 2,4,5-triamino-6-morpholino-pyrimidine, 2,5,6-triamino-4-(dimethylamino)-pyrimidine, 4,5,6-triamino-2-morpholino-pyrimidine, 2,4,5-triamino-6-($\beta$-hydroxyethyl-amino)-pyrimidine, 4,5,6-triamino-2-[($\beta$-aminoethyl)amino]-pyrimidine, 2,5,6-triamino-4-[($\beta$-methylamino)-ethylamino]-pyrimidine, 2,5-diamino-4,6-[bis-($\gamma$-diethylamino) -propylamino]-pyrimidine, 4,5-diamino-6-[($\beta$-hydroxyethyl)-amino]-2-(methylamino)-pyrimidine, 5-amino-2,4,6-(triethylamino)-pyrimidine, and 5-amino-6-anilino-2,4-[bis-($\beta$-hydroxyethyl) ($\beta$-hydroxyethyl)-amino]-pyrimidine.

The above-described tetraaminopyrimidines are disclosed in U.S. Pat. Nos. 4,003,699 and 4,129,413, both of which are incorporated herein by reference. The preparation of most tetraaminopyrimidines to be used as developer components can be taken from the monograph by D. J. Brown, in the series "Heterocyclic Compounds," Interscience Publishers, 1962, Vols. 1 and II, "The Pyrimidines." The preparation of other tetraaminopyrimidines is disclosed in U.S. Pat. Nos. 4,003,699 and 4,129,413. Particularly desirable red-brown tones are obtained with 2,4,5,6-tetraaminopyrimidine and/or derivatives thereof. Additionally, couplers such as p-aminophenol can be employed herein.

The developer components according to the invention can be used either as such or in the form of their water-soluble acid addition salts with non-toxic inorganic acids or organic acids, such as for example, hydrochloric acid, sulfuric acid, phosphoric acid, acetic acid, propionic acid, lactic acid or citric acid.

In addition, the hair coloring preparations according to the invention can contain admixtures of other customary developing components. Besides developer and/or coupler components they can, if desired, also contain customary direct dyestuffs, such as nitrophenylene diamine derivatives. In certain instances, the customary direct dyestuffs are needed for obtaining certain shades; from 0% to about 5% direct dyestuffs may be employed. Examples of couplers which may be included in addition to the coupler of formula I are m-phenylene diamine derivatives, phenols, naphthols, other resorcinol derivatives and pyrazolones. Besides these, other such conventional developers and couplers will be readily perceived by those of ordinary skill in the art.

In the hair dyes according to the invention, the couplers corresponding to formula I and the other coupler substances additionally present, if any, are generally used in substantially molar quantities, based on the developer substances used. Although it has proved best to use molar quantities, there is no disadvantage in using a certain excess of individual oxidation dye precursors.

Furthermore, the developer component, the coupling component, and any direct dyestuffs may be used as pure ingredients or as mixtures. Not only can the developer component consist of mixtures of developers to be used according to the invention, but the coupler substance can also consist of mixtures of the above-mentioned diresorcyl compounds of formula I and mixtures of direct dyestuffs.

The oxidative development of the dye may be carried out with atmospheric oxygen. However, it is preferred to use a chemical oxidizing agent, particularly when, in addition to dyeing, it is desired to lighten or brighten the hair. Representative oxidizing agents include, for example, hydrogen peroxide or addition products of hydrogen peroxide and urea, melamine or sodium borate, as well as mixtures of the addition products of hydrogen peroxide described above with potassium peroxydisulfate. To produce the hair dyes according to the invention, the oxidation dye precursors are incorporated in a suitable cosmetic carrier, such as creams, emulsions, gels, surfactant-containing foaming solutions, for example shampoos, or other preparations suitable for application to hair. Representative standard constituents of cosmetic preparations include wetting agents and emulsifiers, such as anionic, non-ionic or ampholytic surfactants, more specifically, fatty alcohol sulfates, alkane sulfonates, $\alpha$-olefin sulfonates, fatty alcohol polyglycol ether sulfates, alkylbenzenesulfonates, addition products of ethylene oxide and fatty alcohols, fatty acids or alkyl phenols, sorbitan fatty acid esters and fatty acid partial glycerides and fatty acid alkanolamides; thickeners, such as methyl or hydroxymethyl cellulose, starch, fatty alcohols, paraffin oils, and fatty acids; perfume oils and hair-conditioning and grooming additives, such as water-soluble cationic polymers, protein derivatives, panthothenic acid and cholesterol.

The constituents of the cosmetic carriers may be used in the usual quantities in the production of an aqueous preparation of the developer-coupler type for the dyeing of hair in accordance with the invention. For example, emulsifiers may be used in quantities of from 0 to about 30% by weight, preferably from about 0.5 to about 30% by weight, more preferably from about 1 to about 15% by weight, and thickeners may be used in quantities of from 0 to about 25% by weight, preferably from about 0.1 to about 25% by weight, more preferably from about 1 to about 15% by weight, based in each case on the total weight of the hair dye.

The oxidation dye precursors are incorporatied with the constituents of the cosmetic carrier in the aqueous preparation in accordance with the invention in quantities effective to achieve the desired colors. Preferably, the oxidation dye precursors are incorporated in a quantity of developer plus coupler of from about 0.2 to about 5% by weight, preferably from about 1 to about 3% by weight, based on the total weight of the aqueous dye composition. The remainder of the aqueous preparation is water.

The hair dyes according to the invention may be applied in a mildly acidic, neutral or alkaline medium, irrespective of the nature of the cosmetic preparation, i.e., solution, emulsion, cream, gel or shampoo. Preferably, immediately before application to the hair, an oxidizing agent, such as one of those named above, is added to the hair dye.

Hair dyes in accordance with the present invention may be applied at any suitable pH for contact with hair and skin. The preferred pH-range is from about 8 to about 10.

The hair dyes may be applied at any temperature compatible with the consitituents of the hair dye and with the hair and skin of the subject. Preferred temperatures range from about 15° to about 40° C. More preferably, the hair dye is applied at room temperature.

The hair dye is applied to the hair for a time sufficient to impart a sufficient intensity of the desired color shade. Preferably, the application time is from 2-3 minutes to an hour. More preferably, the contact time is approximately 30 minutes.

The hair dye may then be removed from the hair being dyed by rinsing; then the hair is preferably rewashed with a mild shampoo and dried. Rewashing with a shampoo is not needed when a carrier of high surfactant content, for example a dye shampoo, is used.

The dye finishes obtained with hair dyes in accordance with the present invention have a high brilliance and outstanding fastness to heat, light, washing and rubbing. The following Examples are merely illustrative of the present invention without being deemed limitative in any manner.

EXAMPLES

Hair dyes according to the invention were prepared in the form of a cream emulsion having the following composition:

| | |
|---|---|
| $C_{12}$-$C_{18}$ fatty alcohol | 10 g |
| $C_{12}$-$C_{14}$ fatty alcohol + 2 EO-sulfate, Na-salt, 28% | 25 g |

| -continued | |
|---|---|
| water | 60 g |
| coupler substance | 0.0075 mole |
| developer substance | 0.0075 mole |
| $Na_2SO_3$ (inhibitor) | 1.0 g |
| concentrated ammonia solution | up to pH 9.5 |
| water | add to 100 g |

The constituents were mixed with one another in the above order. After addition of the oxidation dye precursors and the inhibitor, the pH-value of the emulsion was initially adjusted to pH 9.5 with concentrated ammonia solution and then made up with water to 100 g.

Oxidative development of the dye was carried out with 3% hydrogen peroxide solution as an oxidizing agent. 50 g of hydrogen peroxide solution (3%) were added and mixed with 100 g of the emulsion.

The cream emulsion dye was applied to approximately 5 cm long strands of standardized, 90% gray, but not specially pretreated, human hair and left for 30 minutes at 27° C. On completion of the dyeing process, the hair was rinsed, washed with a standard shampoo and then dried.

The following compounds were used as coupler substances:

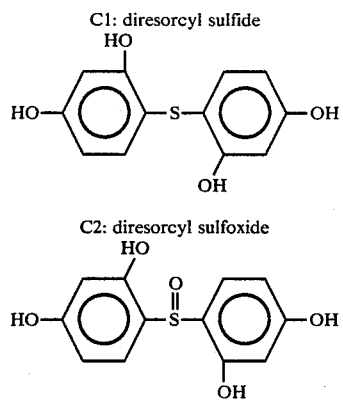

C1: diresorcyl sulfide

C2: diresorcyl sulfoxide

The following compounds were used as developer substances:
D 1: 2,4,5,6-tetraamino pyrimidine
D 2: p-phenylene diamine
D 3: p-tolylene diamine
D 4: 2,5-diaminoanisole
D 5: 2-chloro-o-phenylene diamine
D 6: N-ethyl-N-(2-hydroxyethyl)-p-phenylene diamine
D 7: N,N-dimethyl-p-phenylene diamine
D 8: p-aminophenol.

The dye finishes obtained with these oxidation dye precursors are shown in Table 1:

TABLE 1

| Example | Developer | Coupler | Color obtained |
|---|---|---|---|
| 1 | D 1 | C 1 | red-brown |
| 2 | D 2 | C 1 | dark brown |
| 3 | D 3 | C 1 | dark brown |
| 4 | D 4 | C 1 | dark brown |
| 5 | D 5 | C 1 | olive-brown |
| 6 | D 6 | C 1 | dark brown |
| 7 | D 7 | C 1 | dark brown |
| 8 | D 8 | C 1 | olive-brown |
| 9 | D 1 | C 2 | red-brown |
| 10 | D 2 | C 2 | dark brown |
| 11 | D 3 | C 2 | dark brown |
| 12 | D 4 | C 2 | dark brown |
| 13 | D 5 | C 2 | olive-brown |

TABLE 1-continued

| Example | Developer | Coupler | Color obtained |
|---|---|---|---|
| 14 | D 6 | C 2 | aubergine |
| 15 | D 7 | C 2 | dark brown |
| 16 | D 8 | C 2 | olive-brown |

We claim:

1. A composition of matter of the developer-coupler type for the dyeing of hair comprising:

(a) at least one coupler of the formula

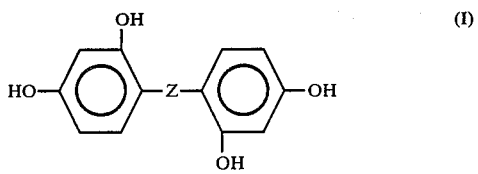

(I)

wherein Z is a sulfur atom, an >SO group or an >SO$_2$ group, or a cosmetically acceptable salt of said coupler of formula I; and (b) at least one developer, said developer being capable of developing a color shade when oxidatively coupled with said coupler of the formula I or with said salt of said coupler.

2. The composition of matter of claim 1, wherein Z is a sulfur atom or an >SO group.

3. The composition of matter of claim 1, wherein said developer is an aromatic diamine or a heterocyclic diamine.

4. The composition of matter of claim 1, wherein said developer is a compound having a 2,4,5,6-tetraaminopyrimidine structure.

5. The composition of matter of claim 1, wherein Z is a sulfur atom or an >SO group and said developer is one or more of 2,4,5,6-tetraaminopyrimidine, p-phenylene diamine, p-tolylene diamine, 2,5-diaminoanisole, 2-chloro-o-phenylene diamine, N-ethyl-N-(2-hydroxyethyl)-p-phenylene diamine, N,N-dimethyl-p-phenylene diamine, and p-aminophenol.

6. The composition of matter of claim 1, further containing at least one additional coupler and at least one direct dyestuff.

7. The composition of matter of claim 1, wherein said developer is one or more of 2,4,5,6-tetraaminopyrimidine, 4,5-diamino-2,6-bis-methyl-aminopyrimidine, 2,5-diamino-4-diethylamino-6-methylaminopyrimidine, 2,4,5-triamino-6-dimethylaminopyrimidine, 2,4,5-triamino-6-piperidinopyrimidine, 2,4,5-triamino-6-anilino-pyrimidine, 2,4,5-triamino-6-morpholinopyrimidine and 2,4,5-triamino-6-(2-hydroxyethyl)-aminopyrimidine.

8. A preparation of the developer-coupler type for the dyeing of hair comprising an effective amount of (a) the composition of matter of claim 1;

(b) at least one additive which is a direct dyestuff, a surfactant, or a thickener.

9. An aqueous preparation of the developer-coupler type for the dyeing of hair, comprising about 0.2% to about 5% by weight of the developer-coupler composition of claim 1; from 0% to about 5% by weight of at least one direct dyestuff; from 0% to about 30% by weight of a surfactant; from 0% to about 25% by weight of a thickener; and water.

10. The aqueous preparation of claim 9 which contains about 1% to about 3% by weight of the developer-coupler composition.

11. The aqueous preparation of claim 9, wherein Z is a sulfur atom or an >SO group.

12. The aqueous preparation of claim 9, wherein said developer is an aromatic diamine or a heterocyclic diamine.

13. The aqueous preparation of claim 9, wherein said developer is a compound having a 2,4,5,6-tetraaminopyrimidine structure.

14. The aqueous preparation of claim 9, wherein Z is a sulfur atom or an >SO group and said developer is one or more of 2,4,5,6-tetraaminopyrimidine, p-phenylene diamine, p-tolylene diamine, 2,5-diaminoanisole, 2-chloro-o-phenylene diamine, N-ethyl-N-(2-hydroxyethyl)-p-phenylene diamine, N,N-dimethyl-p-phenylene diamine, and p-aminophenol.

15. The aqueous preparation of claim 9, further containing at least one additional coupler and at least one direct dyestuff.

16. The aqueous preparation of claim 9, wherein said developer is one or more of 2,4,5,6-tetraaminopyrimidine, 4,5-diamino-2,6-bis-methyl-aminopyrimidine, 2,5-diamino-4-diethylamino-6-methylaminopyrimidine, 2,4,5-triamino-6-dimethylaminopyrimidine, 2,4,5-triamino-6-piperidinopyrimidine, 2,4,5-triamino-6-morpholinopyrimidine and 2,4,5-triamino6-(2-hydroxyethyl)-aminopyrimidine.

17. A process for the dyeing of hair comprising applying to said hair, at temperatures ranging from about 15° C. to about 40° C. for a time sufficient to effect dyeing through oxidation, an effective amount of the developer-coupler composition of claim 1 in an aqueous medium.

18. The process for the dyeing of hair of claim 17, wherein the oxidation is at least in part effected by the action of a chemical oxidizing agent.

* * * * *